United States Patent
Schall et al.

(10) Patent No.: US 9,144,451 B2
(45) Date of Patent: Sep. 29, 2015

(54) SOFT GENERATOR

(75) Inventors: Heiko Schall, Nuertingen (DE); Florian Eisele, Freiburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1146 days.

(21) Appl. No.: 13/062,691

(22) PCT Filed: Aug. 13, 2009

(86) PCT No.: PCT/EP2009/005889
§ 371 (c)(1),
(2), (4) Date: Mar. 25, 2011

(87) PCT Pub. No.: WO2010/025815
PCT Pub. Date: Mar. 11, 2010

(65) Prior Publication Data
US 2011/0172656 A1   Jul. 14, 2011

(30) Foreign Application Priority Data

Sep. 8, 2008  (DE) .......................... 10 2008 046 248
Nov. 4, 2008  (DE) .......................... 10 2008 055 820

(51) Int. Cl.
*A61B 18/10* (2006.01)
*A61B 18/12* (2006.01)
*A61B 18/00* (2006.01)

(52) U.S. Cl.
CPC ... *A61B 18/1233* (2013.01); *A61B 2018/00702* (2013.01); *A61B 2018/00892* (2013.01)

(58) Field of Classification Search
CPC .......... H03H 7/38; A61B 17/39; A61B 18/18; A61B 18/14; A61B 18/1233; A61B 18/1206; A61B 2018/00636; A61B 2018/00642; A61B 2018/00779; A61B 2018/00827; A61B 2018/00892; A61B 2018/1293; A61B 2018/00678; H03L 5/02
USPC .......................................................... 606/34
See application file for complete search history.

(56) References Cited

U.S. PATENT DOCUMENTS

| | | | | |
|---|---|---|---|---|
| 5,442,539 A * | 8/1995 | Cuk et al. | ......................... | 363/89 |
| 5,720,744 A * | 2/1998 | Eggleston et al. | .............. | 606/40 |
| 6,087,902 A * | 7/2000 | Larsson | .......................... | 331/25 |
| 6,246,597 B1 * | 6/2001 | Peron | .............................. | 363/54 |
| 6,325,799 B1 * | 12/2001 | Goble | ............................. | 606/41 |
| 7,429,853 B2 * | 9/2008 | Zhang et al. | .................. | 323/305 |
| 7,609,040 B1 * | 10/2009 | Jain | ................................ | 323/283 |
| 2002/0022836 A1 * | 2/2002 | Goble et al. | .................... | 606/34 |

(Continued)

FOREIGN PATENT DOCUMENTS

| | | |
|---|---|---|
| DE | 39 04 558 A1 | 8/1990 |
| JP | 10-507393 A | 7/1998 |

(Continued)

*Primary Examiner* — Michael Peffley
*Assistant Examiner* — Thomas Giuliani
(74) *Attorney, Agent, or Firm* — Dickstein Shapiro LLP (57) ABSTRACT

A high-frequency surgical generator for generating high efficiency outputs that can be operated in resonance over a wide load resistance range. The high-frequency surgical generator includes a first stage circuit for generating high-frequency power and a second stage circuit coupled to the first state circuit. The second stage circuit includes an input and an output and a series resonant circuit located between the input and the output. The second stage circuit further includes an inductor that is switched parallel to the input and a capacitor that is switched parallel to the output.

7 Claims, 6 Drawing Sheets

(56) References Cited

U.S. PATENT DOCUMENTS

| | | | |
|---|---|---|---|
| 2002/0165531 A1* | 11/2002 | Goble | 606/40 |
| 2003/0153908 A1* | 8/2003 | Goble et al. | 606/41 |
| 2004/0138654 A1* | 7/2004 | Goble | 606/34 |
| 2004/0260279 A1* | 12/2004 | Goble et al. | 606/34 |
| 2005/0177150 A1* | 8/2005 | Amoah et al. | 606/34 |
| 2005/0245921 A1* | 11/2005 | Strul et al. | 606/34 |
| 2006/0025758 A1* | 2/2006 | Strul et al. | 606/32 |
| 2006/0161148 A1* | 7/2006 | Behnke | 606/34 |
| 2006/0238181 A1* | 10/2006 | Luo et al. | 323/282 |
| 2007/0118102 A1 | 5/2007 | Mihori | |
| 2008/0082096 A1* | 4/2008 | Shores et al. | 606/34 |
| 2008/0262490 A1* | 10/2008 | Williams | 606/34 |
| 2008/0294156 A1* | 11/2008 | Newton et al. | 606/34 |
| 2009/0076492 A1* | 3/2009 | Behnke | 606/33 |

FOREIGN PATENT DOCUMENTS

| | | |
|---|---|---|
| JP | 2001-029355 A | 2/2001 |
| JP | 2005-536314 A | 12/2005 |
| WO | WO 96/39085 A1 | 12/1996 |
| WO | WO 98/07378 A1 | 2/1998 |
| WO | WO 2004/030552 A1 | 4/2004 |

* cited by examiner

SOFT GENERATOR

This application claims priority to PCT Application No. PCT/EP2009/005889 filed Aug. 13, 2009, which claims priority to German Patent Application No. 10 2008 046 248.9 filed Sep. 8, 2008 and German Patent Application No. 10 2008 055 820.6 filed Nov. 4, 2008, the disclosures of which are incorporated herein by reference in their entirety.

FIELD OF THE DISCLOSED EMBODIMENTS

The disclosed embodiments relate to a high-frequency surgery generator for generating high efficiency outputs, having a first stage for generating high-frequency power, said first stage being coupled to a second stage, wherein the second stage has an input (A, B) and an output (C, D), and wherein a series resonant circuit is located between the input (A, B) and the output (C, D) of the second circuit.

BACKGROUND

The constant development of high-frequency surgery in recent years has led to procedures for contact coagulation (tumor devitalization), to methods for (underwater) tissue sections and for (underwater) tissue vaporization. High-frequency generators which operate with high continuous outputs and very high pulse outputs and/or long activation times are used to perform these procedures. At the same time, however, requirements on the electromagnetic compatibility (EMC) of the high-frequency generators used are increasing because interference with other electromedical apparatus, for patient monitoring or diagnosis for example, is becoming increasingly unacceptable. As a result, the measures necessary to ensure the inherent interference immunity of such high-frequency generators, which nevertheless achieve the high high-frequency outputs required, can only be implemented with a significant amount of technical development effort.

It is known from the prior art to use circuit arrangements including series and/or parallel resonant circuits for the generation of high-frequency power which are fed by power semiconductors in switched mode. For the output characteristics of the high-frequency generators, alongside the properties of the power supply unit (including any closed-loop control systems), the crucial factors are primarily the design of these resonant circuits and the manner in which they are fed, which may also serve as a control variable for closed-loop control circuits. At the same time, it is known that the resonant frequency and the input resistance (and hence the transformation ratio of such resonant circuits) are essentially dependent on the load resistance. In the circuit arrangements known from the prior art for the implementation of high-frequency generators with resonant circuits, this leads to the resonance splitting at a specific frequency, depending on the operating mode, since the series and parallel resonant circuits interact with each other above a certain load resistance range. However, unfavorably high power supply unit currents would be needed, among other things, in order to still achieve the high power output required. On one hand this has an adverse effect on the high-frequency generator's efficiency and on the other it leads to operation of the high-frequency generator with non-sinusoidal input current as a result of which the EMC characteristics of the high-frequency generator also deteriorate.

Figure 4A:
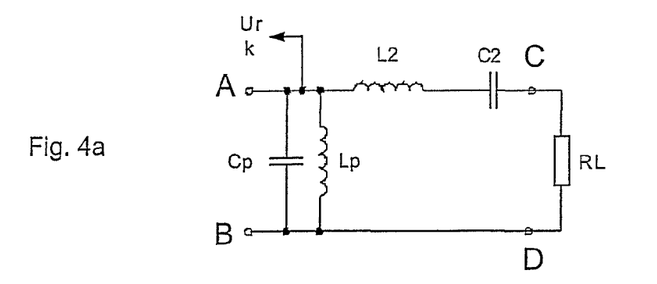
FIGS. 4a-4c illustrate a circuit diagram of a resonant circuit for generating high-frequency output having an input parallel resonant circuit and the associated curves of various output variables, known from the prior art.
Figure 5A:
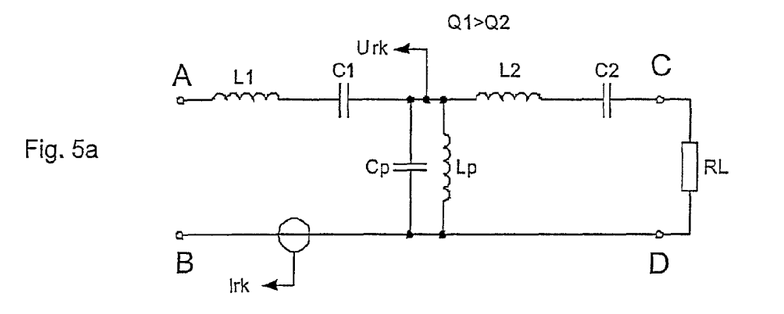
FIGS. 5a-5c illustrate a circuit diagram of a resonant circuit for generating high-frequency output having an input series resonant circuit and the associated curves of various output variables, known from the prior art.

FIG. 4a and FIG. 5a illustrate circuit diagrams of different resonant circuits known from the prior art, such as are used for generating high-frequency power outputs. In these cases, it is possible to integrate a (leakage) transformer using the structure $L_p$, $L_2$ for an additional impedance transformation which is independent of the load resistance.

Figure 4B:
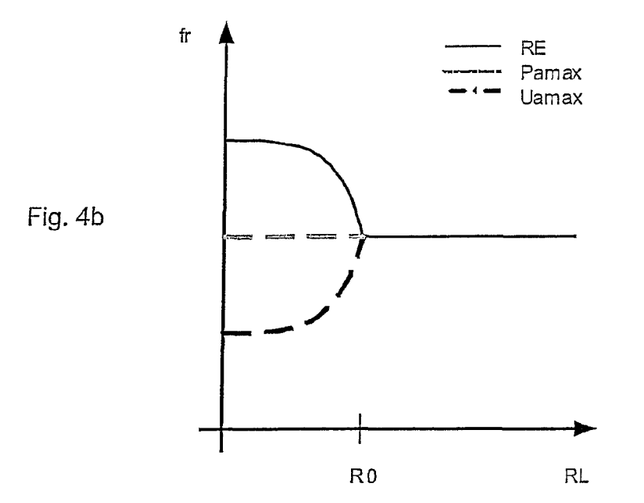
Figure 4C:
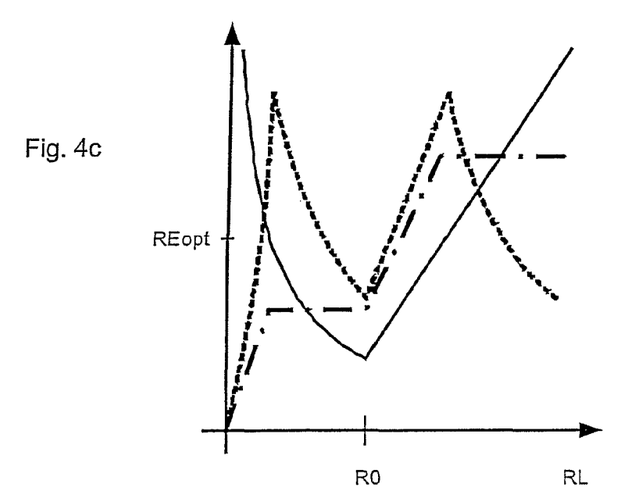
Figure 5B:
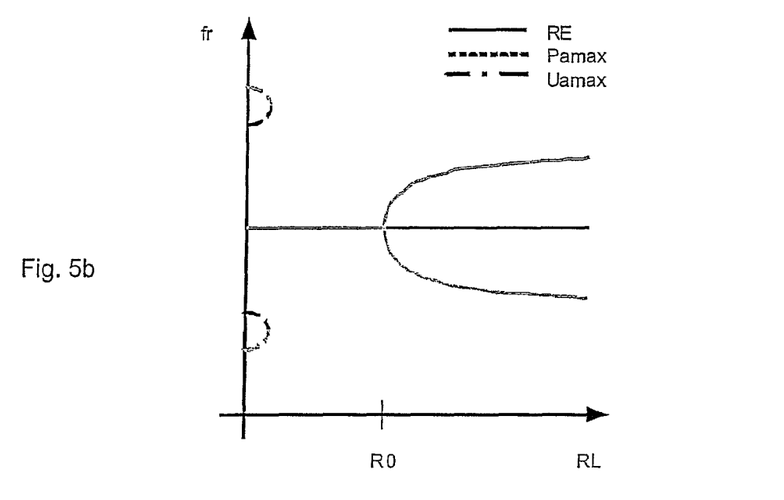

FIG. 4b, c and FIG. 5b, c illustrate the curves of the resonant frequency $f_r$, the filter input resistance RE and the maximum output $P_{a,max}$ and output voltage $U_{a,max}$ associated with each circuit diagram as a function of the load resistance RL. Both of the latter additionally depend on the type of supply.

In this case, a supply with a square-wave voltage of the corresponding resonant frequency and a power supply unit with a maximum output voltage $U_0$ and a maximum output current $I_0$ is assumed. Under these conditions, the optimum load resistance $R_{opt}=U_0/I_0$ transforms into the optimum filter input resistance $RE_{opt}=8/pi^2*R_{opt}$.

The power supply unit operates in the current limiting for $RE<RE_{opt}$ and in the voltage limiting for $RE>RE_{opt}$. In accordance with the properties of ideal resonance circuits, resonance points at which the filter behaves like a series resonant circuit (SRC) or parallel resonant circuit (PRC) are described as series resonances (SR) or parallel resonances (PR). FIG. 4b, c and FIG. 5b, c illustrate series resonances by means of a broken line and parallel resonances by means of a continuous line.

Figure 5C:
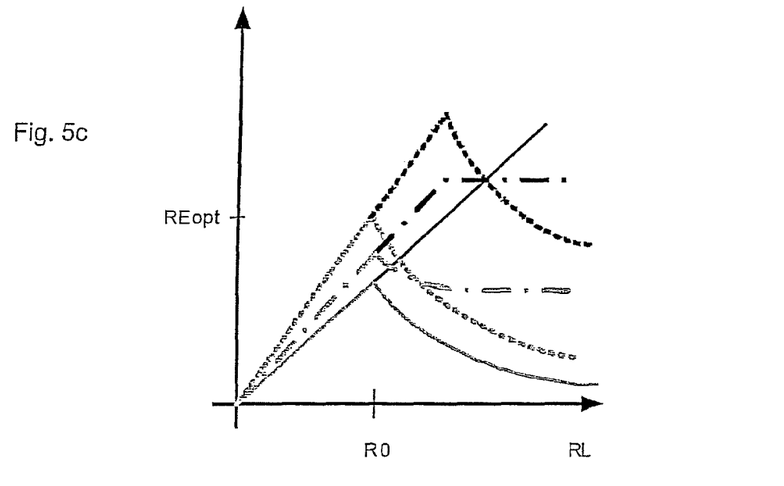

In addition, FIGS. 4b and 5b each illustrate all the resonance points possible for the filter, but only the operating frequencies actually occurring with the type of frequency feedback chosen in each case are represented by means of a continuous line. In FIGS. 4c and 5c, the filter input resistance RE is represented only for these frequencies by means of a continuous line, the maximum output $P_{a,max}$ by means of a broken line and the maximum peak output voltage $U_{amaxp}$ by means of a dot-dash line.

The loaded qualities of the individual resonance circuits $Q1=1/RL*sqrt(L1/C1)$, $Q2=1/RL*sqrt(L2/C2)$ and $Qp=RL*sqrt(Cp/Lp)$ are helpful for characterizing the curve shapes.

Branching of the resonant curves takes place at load resistance $R_o$ which emerges in FIG. 4b from $Qp=Q2$ and in FIG. 5b from $Qp=Q1+Q2$. As illustrated here, branching then takes place at precisely the point when the resonant frequencies of the individual resonant circuits coincide.

FIG. 4a shows a resonant circuit known from the prior art for generating outputs having a parallel resonant circuit (PRC) at input A, B comprising a capacitor $C_p$ and an inductor $L_p$, a series resonant circuit having an inductor $L_2$ and capacitor $C_2$ and a load $R_L$, at output C, D. In conjunction with the voltage supply usually used, this arrangement is unsuitable for fulfilling the requirements for high high-frequency output and a good level of efficiency because a highly non-sinusoidal input current appears in the process. Although a current supply would remedy matters appropriately, supplying by using a power source is, however, comparatively complex.

It is apparent from FIG. 4b that the resonant frequency for small load resistances splits because the parallel resonant circuit PRC and the output series resonant circuit SRC interact. As a result, the resonant frequency increases as the load resistance decreases.

FIG. 5a shows a resonant circuit known from the prior art for generating outputs having a series resonant circuit SRC at input A, B comprising an inductor $L_1$ and a capacitor $C_1$, a parallel resonant circuit PRC having a capacitor $C_p$ and an inductor $L_p$, a series resonant circuit SRC having an inductor $L_2$ and a capacitor $C_2$ and a load $R_L$, at output C, D.

Although this circuit configuration is suitable for a voltage supply, it has the drawback that the series resonance splits for large load resistances and shifts severely as a result as is apparent from FIG. 5b since the input SRC and PRC interact with each other and at the same time the associated input resistances assume such small values that unfavorably large power supply currents would be necessary in order to achieve the desired output. It is necessary to switch over to parallel resonance to prevent this. However, this leads to an operating mode with non-sinusoidal input current which would have a negative impact on the EMC characteristics of the arrangement:

As explained above, the measures known from the prior art for minimizing the drawbacks referred to have therefore consisted so far in providing the circuit arrangement of an high-frequency generator with either a current or a voltage supply depending on the application. However, the circuit engineering required to implement this solution is frequently complex.

SUMMARY

The object of the disclosed embodiments is thus to develop a high-frequency generator for the generation of outputs in such a manner that the problems and drawbacks known from the prior art and discussed above can be minimized and in particular that a high efficiency high-frequency output can be achieved at the same time in the widest load resistance range possible with good EMC characteristics.

This object is achieved by a high-frequency generator having an inductor ($L_p$) switched parallel to the input (A, B) and a capacitor ($C_p$) switched parallel to the output (C, D) so that the high-frequency generator can be operated in resonance over a wide load resistance range.

In the disclosed embodiments, the parallel inductor at the input prevents the effect of a parallel resonant circuit (PRC) otherwise normally used in its place and therefore prevents splitting of the resonances at a specific operating frequency. Further, the capacitor that is switched parallel to the output guarantees a series resonance even over a wide load resistance range.

In a particular implementation of the high-frequency generator, it is envisaged that the output capacitor $C_p$ has a capacitance that is high in amount compared to the capacitance of a capacitor $C_2$ of the series resonant circuit. This dimensioning makes it possible for the generator frequency to have only a low dependence on the load resistance. There is also no occurrence of any particularly significant dependence of the high-frequency generator characteristics under varying capacitive load due to the absolute size of the output capacitor $C_p$ compared to capacitive loads arising in practice, such as are brought about, for example, by output leads or endoscopes.

In a further embodiment of the high-frequency generator, it is envisaged that the first stage generates a square-wave voltage, the phase position of which is synchronized with an input current flowing into the input (A, B) of the second stage. This ensures that the high-frequency generator can be operated in resonance in the chosen load resistance range and that zero voltage and zero current switching (ZVS and ZCS) of the power semiconductors is guaranteed by means of minimum inductive detuning. In this case, phase synchronization may be implemented simply using a PLL circuit.

The high-frequency generator according to the disclosed embodiments may have a voltage regulator for monitoring an output voltage $U_A$ at the output (C, D) of the second stage. This is because the maximum output voltage, particularly for large load resistances, rises steeply and this must be prevented by means of an appropriate circuit arrangement. One, but not limited to one, possibility is to reduce the power supply voltage accordingly. The voltage regulator may therefore be used to regulate a power supply unit which supplies the first stage.

In another embodiment, it is envisaged that an overvoltage protector, such as for example a varistor, is inserted between the point of attachment of $L_2$ and $C_2$ and of the patient mass (D or B). In this manner, it is ensured that, in the event of a sudden drop in load, the output voltage $U_A$ is limited to uncritical values until a corrective controller action becomes effective to protect against overvoltage.

In another embodiment, a surgical system with a high-frequency surgery generator having a surgical instrument for the treatment of tissue that represents a load ($R_L$) with a capacitive component, said load being present at an output (C, D) of the second stage. At the same time, the capacitance of the output capacitor ($C_p$) is high in amount compared to the capacitive component of the load ($R_L$). Such dimensioning ensures that the surgical system with the high-frequency surgery generator can be operated in resonance over a wide load resistance range. In addition, a reduction is achieved in the dependence of the generator characteristics under varying capacitive load.

BRIEF DESCRIPTION OF THE DRAWINGS

The disclosed embodiments will be described in greater detail, pointing out further features and advantages, by reference to the example embodiments illustrated in the drawings

DETAILED DESCRIPTION

In the following description, the same reference numbers are used for the same and similarly acting parts.

Figure 1A:
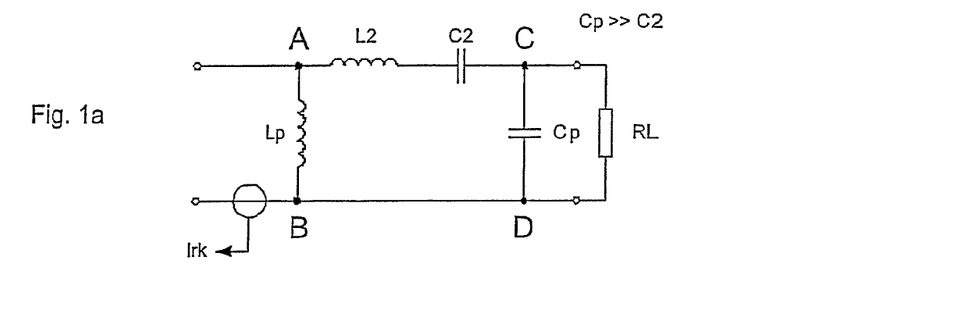
FIGS. 1a-1c illustrate a circuit diagram of a resonant circuit for generating high-frequency power and the associated curves of various output variables in accordance with the disclosed embodiments.
Figure 1B:
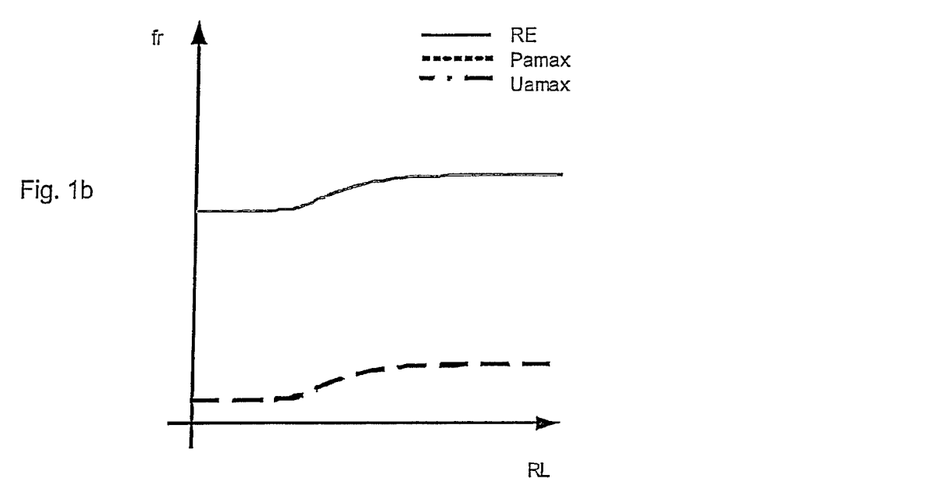
Figure 1C:
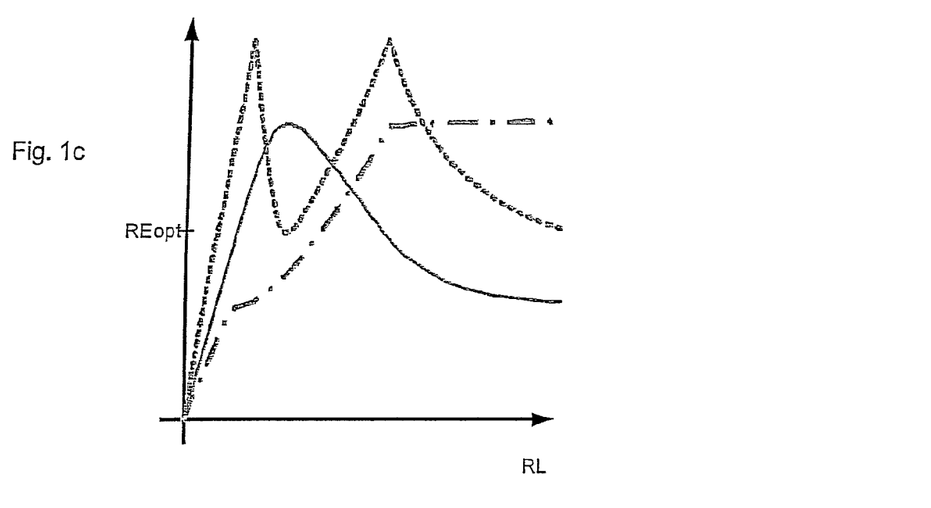

FIG. 1a illustrates a resonant circuit according to a disclosed embodiment having an inductor $L_p$ parallel to input A, B, a series resonant circuit SRC having an inductor $L_2$ and capacitor $C_2$ and a capacitor $C_p$ and a load $R_L$, parallel to output C, D.

The drawbacks of the circuit configurations described in FIG. 4a and FIG. 5a (and others known from the prior art) may be avoided using the circuit configuration according to FIG. 1a by replacing the effect of a PRC with the parallel inductor $L_p$ and therefore preventing splitting of the resonances. Operation of the circuit in series resonance is also guaranteed for large load resistances $R_L$ by the additional insertion of capacitor $C_p$. An input SRC is then no longer absolutely necessary. In an existing transformer, series resonant capacitor $C_2$ may be partially relocated and series resonant inductor $L_2$ may even be relocated completely to its primary side allowing for the transformation ratio. The circuit configurations that arise due to relocation of series dummy elements $C_2$ and $L_2$ to the primary side of a transformer do not in principle exhibit any other characteristics and are to be considered as acting in an identical manner within the meaning of the disclosed embodiments.

The circuit presented in FIG. 1a has a continuous series resonance, the load characteristic of which can be kept low if $C_p >> C_2$ is selected. This embodiment of the resonant circuit may, for example, be operated in resonance over the entire load resistance range by means of a square-wave voltage generated using a half or full bridge, the phase position of which is synchronized with the filter input current. Zero voltage and zero current switching (ZVS and ZCS) of the power semiconductors is guaranteed by means of minimum inductive detuning. Phase synchronization may be implemented simply using a PLL circuit.

Alternatively, resonant operation may also be guaranteed with direct feedback of the current signal to the drive circuit. An output signal with a very low level of distortion is generated by means of symmetrical, continuous control. This allows the evaluation of harmonics as a measuring variable for tissue characteristics and for ensuring high process quality.

In addition, it is possible, by means of suitable dimensioning, to achieve high outputs (particularly at small load resistances) and therefore high output currents such as are required, for example, for procedures in urology and for bipolar coagulation of vessels. At the same time, it is possible to implement a relatively large filter input resistance for the entire relevant load resistance range, particularly for the upper range. As a result there is no need for any particularly high power supply unit currents. This is an essential requirement for high efficiency.

Favorable EMC behavior of the high-frequency generator can be guaranteed as a result since zero voltage and zero current switching (ZCS and ZVS mode) of the power semiconductors is possible and a sinusoidal input current appears over the entire operating range.

Figure 2:
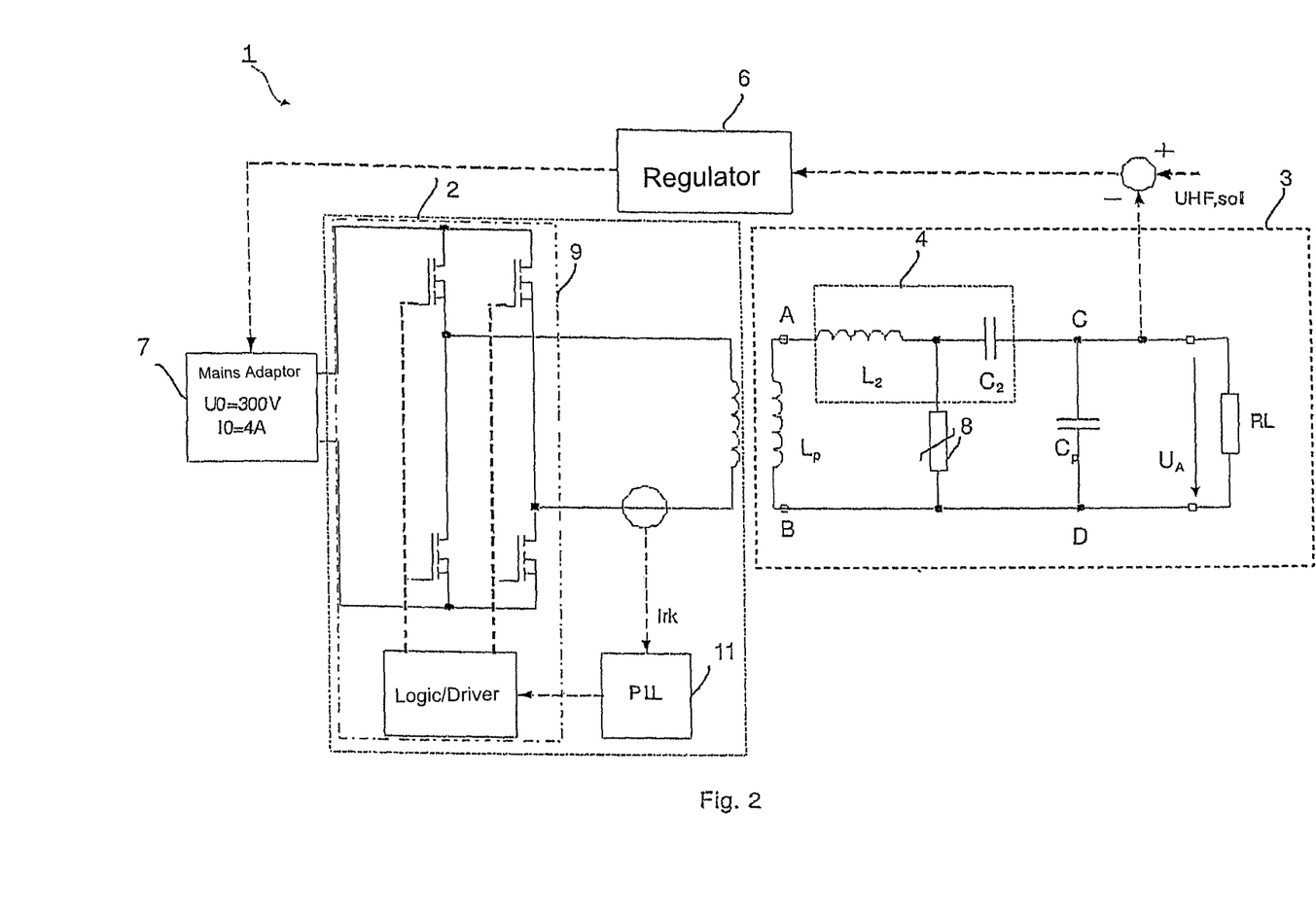
FIG. 2 illustrates a detailed circuit of an example embodiment.

FIG. 2 shows an example embodiment for a high-frequency generator. The high-frequency generator 1 shown in FIG. 1 includes a power supply unit 7 and a first stage 2 which is coupled to a second stage 3. In the example embodiment illustrated, first stage 2 has a driver stage 9 which is configured as a full bridge and generates a square-wave voltage and a PLL circuit 11 for phase synchronization of the square-wave voltage generated by the driver stage with an input current $I_{rk}$. Second stage 3 has an input A, B and an output C, D and a series resonant circuit 4 having an inductor $L_2$ (200 µH) and a capacitor $C_2$ (1 nF) is located between the input A, B and the output C, D of the second stage 3. An inductor $L_p$ (196 µH) is situated parallel to output C, D, a capacitor $C_p$ (4 nF) is arranged parallel to output C, D and a load $R_L$ is switched parallel to output C, D. An overvoltage protector 8 having an overvoltage protection for voltages up to 1 kV (which may, for example, be configured as a varistor) is located between the point of connection of $L_2$ and $C_2$ and output D.

Output voltage $U_A$ at output C, D is monitored via a voltage regulator 6. In the event of a sudden drop in load, overvoltage protector 8 first limits output voltage $U_A$ to uncritical values until a corrective controller action becomes effective. The illustrated embodiment envisages that voltage regulator 6 regulates power supply unit 7, which supplies first stage 2, via fed back output voltage $U_A$.

Figure 3A:
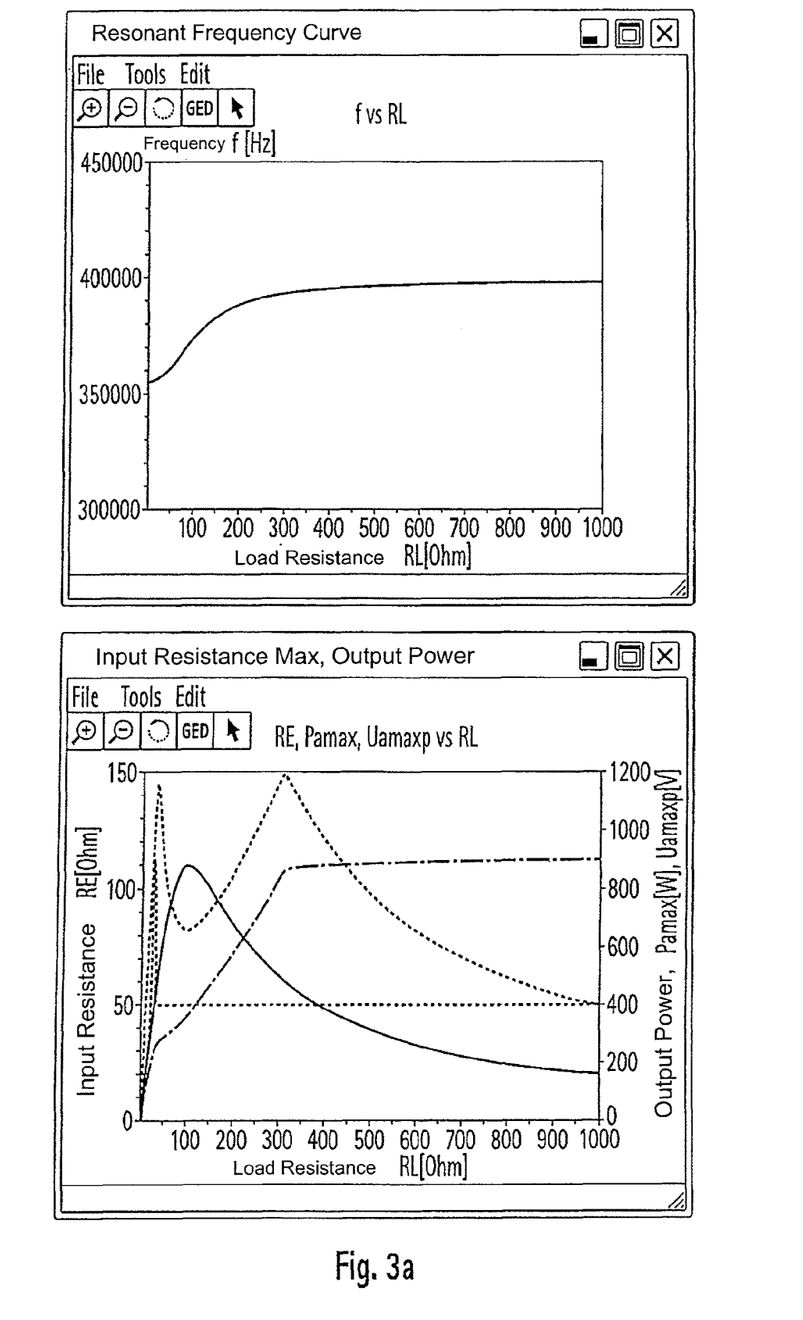
FIGS. 3a-3b illustrate a resonant frequency curve and the output characteristic of the high-frequency generator according to the embodiment of FIG. 2.
Figure 3B:
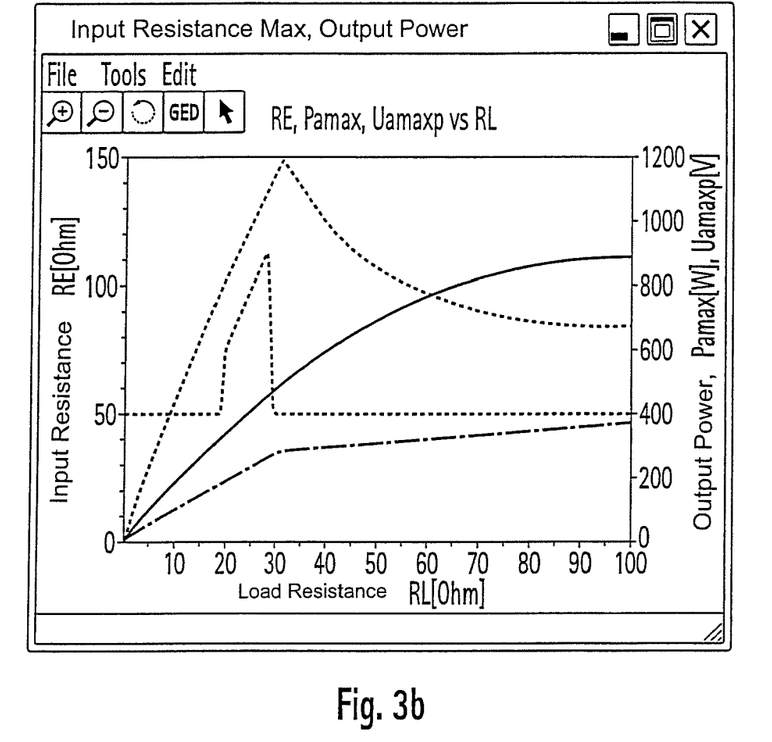

FIG. 3a and FIG. 3b show the resonant frequency curve and the output characteristic of the high-frequency generator illustrated in FIG. 2. FIG. 3b shows an expanded diagram of the lower load resistance range shown in FIG. 3a. The parameters of the power supply unit used as the basis for the output characteristic are $U_0=300V$ and $I_0=4$ A. The optimum filter input resistance for max. output results in: $RE_{opt}=60.8\ \Omega$.

The generator frequency is only dependent on the load resistance to a small extent since the capacitor $C_p$ at output C, D is chosen to be large compared to the capacitor $C_2$ of the series resonant circuit. No significant dependence of the generator characteristics occurs under varying capacitive load since the capacitor $C_p$ is chosen to be large compared to capacitive loads arising in practice (due to output leads or endoscopes). This is favorable for the design of a PLL circuit and simplifies measurement and evaluation of the output signals. A tolerance pattern for the output, such as is the aim for a generator for bipolar transurethral resection (TUR), is plotted using a broken line in FIG. 3a. One can see that the tolerance pattern is fulfilled in the expanded diagram of the lower load resistance range of FIG. 3b.

It should be noted at this point that all the aforementioned parts are claimed as essential to the invention both alone and in any combination, particularly the details shown in the drawings. Amendments thereof are the common practice of persons skilled in the art.

The invention claimed is:

1. A high-frequency surgical generator for generating high efficiency outputs, the high-frequency surgical generator comprising:
    a first stage circuit for generating high-frequency power; and
    a second stage circuit coupled to said first stage circuit, wherein the second stage circuit comprises:
        an input and an output;
        a series resonant circuit located between the input and the output;
        an inductor switched parallel to the input; and
        an output capacitor switched parallel to the output,
        wherein the configuration of the second stage circuit allows the high-frequency surgical generator to be operated in resonance over a wide load resistance range, and
        wherein the output capacitor has a capacitance that is higher than a capacitance of a capacitor of the series resonant circuit.

2. The high-frequency surgical generator according to claim 1, wherein the first stage circuit generates a square-wave voltage, the phase position of which is synchronized with an input current flowing into the input of the second stage circuit.

3. The high-frequency surgical generator according to claim 1, further comprising a voltage regulator for monitoring an output voltage at the output of the second stage circuit.

4. The high-frequency surgical generator according to claim 3, wherein the voltage regulator is configured to regulate a power supply unit which supplies the first stage circuit.

5. The high-frequency surgical generator according to claim 1, wherein the second stage circuit further comprises an overvoltage protector so that an output voltage of the second stage is limited in the event of a sudden drop in load, thereby protecting against overvoltage.

6. The high-frequency surgical generator according to claim 5, wherein the overvoltage protector is a varistor.

7. A surgical system comprising:
    the high-frequency surgical generator according to claim 1; and
    a surgical instrument for the treatment of tissue,
    wherein the tissue represents a load with a capacitive component,
    wherein said load is adapted to be present at the output of the second stage circuit, and wherein the capacitance of the output capacitor is higher than the capacitive component of the load.

* * * * *